(12) United States Patent
Valadkhan (10) Patent No.: US 9,308,218 B2
(45) Date of Patent: Apr. 12, 2016

(54) COMPOSITIONS AND METHODS FOR TREATING CANCER

(71) Applicant: Case Western Reserve University, Cleveland, OH (US)

(72) Inventor: Saba Valadkhan, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 104 days.

(21) Appl. No.: 14/212,639

(22) Filed: Mar. 14, 2014

(65) Prior Publication Data

US 2014/0275217 A1    Sep. 18, 2014

Related U.S. Application Data

(60) Provisional application No. 61/781,969, filed on Mar. 14, 2013.

(51) Int. Cl.

| | | |
|---|---|---|
| *C07H 21/02* | (2006.01) | |
| *C07H 21/04* | (2006.01) | |
| *A61K 31/70* | (2006.01) | |
| *A61K 31/713* | (2006.01) | |
| *A61N 5/10* | (2006.01) | |
| *C12N 15/113* | (2010.01) | |
| *A61K 45/06* | (2006.01) | |
| *A61K 31/7105* | (2006.01) | |
| *C12Q 1/68* | (2006.01) | |
| *A61F 7/00* | (2006.01) | |
| *A61N 7/02* | (2006.01) | |
| *A61B 18/12* | (2006.01) | |
| *A61B 19/00* | (2006.01) | |

(52) U.S. Cl.
CPC ............ *A61K 31/713* (2013.01); *A61K 31/7105* (2013.01); *A61K 45/06* (2013.01); *A61N 5/10* (2013.01); *C12N 15/113* (2013.01); *A61B 18/12* (2013.01); *A61B 2019/5236* (2013.01); *A61F 7/00* (2013.01); *A61N 7/02* (2013.01); *A61N 2005/1098* (2013.01); *C12N 2310/14* (2013.01); *C12N 2310/531* (2013.01)

(58) Field of Classification Search
None
See application file for complete search history.

(56) References Cited

U.S. PATENT DOCUMENTS

2012/0183511 A1* 7/2012 Valadkhan et al. ......... 424/93.21

OTHER PUBLICATIONS

Takeda et al. The Journal of Biological Chemistry vol. 273(27):17079-17086, 1998.*

* cited by examiner

*Primary Examiner* — Sean McGarry
(74) *Attorney, Agent, or Firm* — Tarolli, Sundheim, Covell & Tummino LLP (57) ABSTRACT

A method of treating a BORG expressing cancer includes administering a therapeutically effective amount of at least one BORG inhibiting agent to the BORG overexpressing cancer cells of the subject.

16 Claims, 4 Drawing Sheets

COMPOSITIONS AND METHODS FOR TREATING CANCER

RELATED APPLICATION

This application claims priority from U.S. Provisional Application No. 61/781,969 filed Mar. 14, 2013, the subject matter of which is incorporated herein by reference in its entirety.

TECHNICAL FIELD

This application relates to methods and compositions for treating cancer.

BACKGROUND

Recent analyses of the transcriptional output of mammalian genomes have revealed the presence of a significant number of novel long non-protein-coding (lnc) RNAs. Although many lncRNAs show a tissue or developmental stage-specific expression pattern that is conserved across different species, the question of whether the majority of this class of transcripts have any cellular function whatsoever remains the subject of intense debate. Most mysterious are the long intergenic non-coding RNAs, a class of transcripts derived from genomic regions located far away from known genes, which have remained highly understudied.

Interestingly, a substantial fraction of the cellular lncRNAs, including intergenic lncRNAs, are expressed in the brain and other neural tissues. Although few studies have addressed the roles of these transcripts in the development and function of the nervous system, current data point to diverse regulatory functions for lncRNAs in brain, ranging from regulating expression of homeobox proteins and development of neuronal GABAergic circuitry to regulating biogenesis of RNAs involved in synaptic function. Although these studies, together with analyses of lncRNA function in non-neuronal cells, suggest that this class of RNA molecules participates in virtually every aspect of cellular function, the overall importance of lncRNA-mediated regulation for cellular and organismal function remains controversial.

SUMMARY

Embodiments described herein relate to a method of treating a subject suffering from a cancer that overexpresses BORG RNA. The method includes administering a therapeutically effective amount of at least one BORG inhibiting agent to BORG overexpressing cancer cells of the subject. In some aspects, the therapeutically effective amount can be an amount effective to inhibit NFkB activation in the cancer cells. In some embodiments, the therapeutically effective amount can be the amount effective to inhibit expression and/or induction of c-MET in the cancer cells. In certain aspects, the BORG inhibiting agent can include a RNA interference construct against BORG RNA.

In some aspects, the cancer can be selected from the group consisting of lung cancer, breast cancer, brain cancer and cervical cancer. In some, aspects the cancer cells can include primary tumor cells or metastatic tumor cells overexpressing BORG RNA.

BRIEF DESCRIPTION OF THE DRAWINGS

The foregoing and other features of the present application will become apparent to those skilled in the art to which the present application relates upon reading the following description with reference to the accompanying drawings, in which:

FIGS. 1(A-B) illustrate graphs showing BORG overexpression results in strong induction of the c-MET proto-oncogene and the NFkB pathway: (A) the levels of BORG and c-MET in vector transfected (+vector) and BORG overexpressing cells (+BORG); (B) the level of the regulatory subunit of IKK, the inducer of the NFkB pathway in BORG overexpressing cells.

FIGS. 3(A-B) illustrate graphs showing that BORG expression level is increased in the most aggressive cancers: (A) is the level of BORG in a set of three mouse breast cancer cell lines (67NR, 4T07, and 4T1) having an increasing level of malignancy cultured in rigid and compliant three dimensional culture systems, normal lung epithelium (NL20), primary tumor cells (A549) and metastatic tumor cells (H1650); and (B) the level of BORG expression in response to TGFb in mammary epithelial cells transformed with EGFR.

FIGS. 4(A-J) illustrate graphs showing that BORG is induced in response to stress and is necessary for post-stress survival: (A)-(C) show the induction of the level of expression of BORG as determined by RT-qPCR in response to heat shock in N2a mouse neuroblastoma cells, C3H10 mouse fibroblasts, primary mouse fibroblasts, mouse myoblast C2C12 cells, and human HeLa cells; (D) Induction of BORG in C2C12 cells shown by in situ hybridization; (E)-(F) show that BORG is also induced in response to oxidative stress in both N2A and C2C12 cells (RT-qPCR assays); (G) shows that BORG is also induced in response to ER stress (induced by addition of Thapsigargin, TG); (H) shows the level of overexpression and knock down of BORG in cell lines transfected by a BORG expression vector or a vector expressing an shRNA against BORG (RT-qPCR assay); (I) indicates that overexpression of BORG almost completely blocks post-stress cell death, as shown by MTT cell survival assays in C2C12 cells. While vector transfected, control cell lines show close to 50% cell death after an hour long heat shock or oxidative stress, the BORG overexpressing cells are almost 100% alive; (J) shows that while vector transfected cells or control cells transfected with a non-specific shRNA show ~50%-30% survival after heat stress (in C2C12 and N2A cells, respectively), the survival level of BORG knock down cells is ~5%.)

FIG. 5 illustrates: (A) the level of expression of BORG in four stable knock down C2C12 cell lines vs. controls. Each RT-PCR experiment is performed at least three times, and the error bars represent two standard deviations; (B) In situ hybridization indicating the loss of nuclear signal in cells transfected with shRNA construct against BORG (shRNA 80-2). The cells studied in each panel and the in situ hybridization probe used is shown on top of each image; and (C) Phase contrast image depicts BORG knock down C2C12 cells stably transfected with shRNA 80.

DETAILED DESCRIPTION

All scientific and technical terms used in this application have meanings commonly used in the art unless otherwise specified. The definitions provided herein are to facilitate understanding of certain terms used frequently herein and are not meant to limit the scope of the present invention.

As used herein, the term "subject" refers to any mammal including but not limited to human, non-human primate, cow, horse, pig, sheep, goat, dog, cat or rodent.

As used herein, the term "neoplastic disorder" refers to a disease state in a subject in which there are cells and/or tissues which proliferate abnormally. Neoplastic disorders can include, but are not limited to, cancers, sarcomas, tumors, leukemias, lymphomas, and the like.

As used herein, the term "neoplastic cell" refers to a cell that shows aberrant cell growth, such as increased, uncontrolled cell growth. A neoplastic cell can be a hyperplastic cell, a cell from a cell line that shows a lack of contact inhibition when grown in vitro, a tumor cell, or a cancer cell that is capable of metastasis in vivo. Alternatively, a neoplastic cell can be termed a "cancer cell." Non-limiting examples of cancer cells can include lymphoma cells, melanoma cells, sarcoma cells, leukemia cells, retinoblastoma cells, hepatoma cells, myeloma cells, glioma cells, mesothelioma cells, carcinoma cells and adenocarcinoma cells.

As used herein, the term "tumor" refers to an abnormal mass or population of cells that result from excessive cell division, whether malignant or benign, and all pre-cancerous and cancerous cells and tissues.

As used herein, the terms "treating" or "treatment" refer to executing a treatment protocol, which may include administering a BORG inhibiting agent to a cancer cell in a subject and then treating the cancer cell with an anti-cancer agent to eradicate at least one cancer cell, tumor cell or microorganism. Thus, "treating" or "treatment" does not require complete eradication of cancer and tumor cells or microorganisms.

As used herein, the terms "radiation therapy" or "radiotherapy" refers to the use of high-energy radiation from x-rays, gamma rays, neutrons, protons, and other sources to kill cancer cells and shrink tumors. Radiation may come from a machine outside the body (external-beam radiation therapy), or it may come from radioactive material placed in the body near cancer cells (internal radiation therapy). Systemic radiation therapy uses a radioactive substance, such as a radiolabeled monoclonal antibody, that travels in the blood to tissues throughout the body. The terms are intended to include without limitation ionizing radiation therapy, brachytherapy, sealed source radiation therapy, systemic radioisotope therapy, unsealed source radiotherapy, radionuclide therapy, external beam radiation therapy, radiation surgery, charged-particle radiotherapy, neutron radiotherapy, x-ray therapy, and cobalt therapy.

As used herein, the term "ionizing radiation" means radiation comprising particles or photons that have sufficient energy or can produce sufficient energy via nuclear interactions to produce ionization (gain or loss of electrons). An exemplary ionizing radiation is an x-radiation or gamma-radiation.

As used herein, the term "cell-sensitizing composition" refers to a composition comprising a BORG inhibiting agent described herein capable of increasing sensitivity or reducing resistance to stress. In some aspects, a "cell-sensitizing composition" refers to a composition comprising. By "sensitizing" it is meant that the cell exhibits an increased sensitivity or reduced resistance to stress. For example, increased sensitivity or reduced resistance of a tumor cell may be measured according to methods known in the art, e.g., cell proliferative assays, tumor volume reduction or a reduction in the rate of tumor volume increase.

Embodiments described herein relate to methods and compositions for treating diseases, disorders, and conditions where inhibition of BORG long non-coding RNA activity is desired. The methods can include administering to cells at least one agent that inhibits BORG RNA expression and/or activity in the cells.

Figure 2:
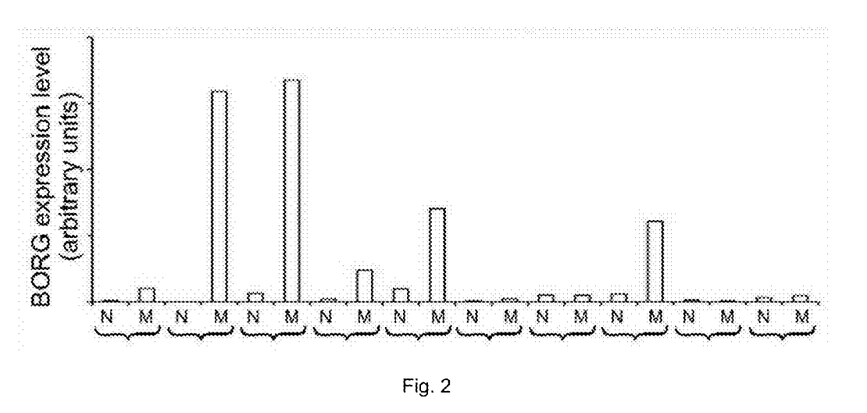
FIG. 2 is a graph showing the BORG expression level in ten pairs of tumor tissue (M) and adjacent normal lung tissue (N) from non-small cell lung cancer patients.
Figure 3A:
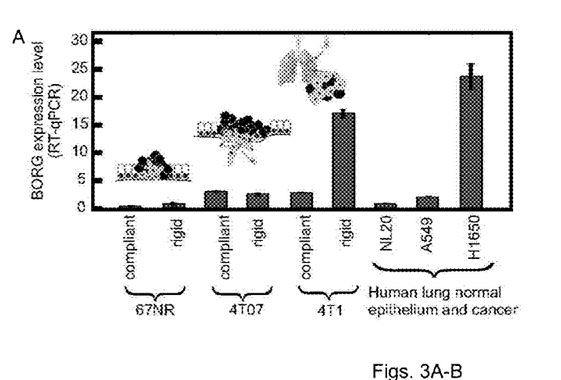
Figure 3B:
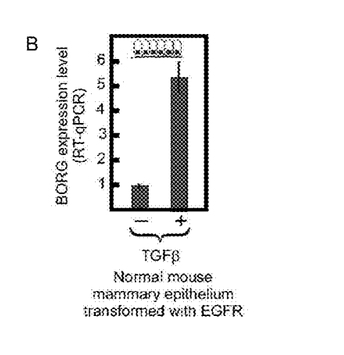

It was found that BORG RNA is induced in response to multiple stress types and is necessary for post-stress survival (FIG. 4) in multiple cell lines, suggesting the generality of the protective effect of BORG RNA against cell death. In addition it was found that BORG RNA expression is greater in cancer tissue compared to adjacent normal tissue in the same subject (FIG. 2) and that BORG RNA expression is increased in the most aggressive cancers, such as metastatic cancers (FIG. 3). It was also found that BORG RNA overexpression in eukaryotic cells results in strong induction of the c-MET proto-oncogene and increases the expression of IKK, the inducer of the NFkb pathway in cells (FIG. 1), suggesting that BORG RNA expression not only has a major role in differentiation of pluripotent cells and primary neuronal progenitors into neurons but also has a major role in cancer and cancer progression.

BORG RNA can therefore be used as a target for the treatment of a cancer, such as a cancer associated with the overexpression of BORG RNA. Accordingly, based at least in part on these findings, in some embodiments of the application cancer cells of a subject overexpressing BORG long non-coding RNA, can be contacted with a therapeutically effective amount of an agent that inhibits BORG RNA expression or inhibits BORG RNA activity (i.e., a BORG inhibiting agent) in the cancer cells. As used herein, the term "BORG inhibiting agent" refers to a polypeptide, polynucleotide, or small molecule capable of substantially reducing or inhibiting the expression and/or activity of BORG in a cancer cell.

By inhibiting or substantially reducing the expression and/or activity of BORG, it is meant that the expression and/or activity of BORG RNA may be entirely or partly diminished. For example, an inhibition or reduction in the expression and/or functioning of BORG RNA may prevent induction of the c-MET proto-oncogene or NFkB pathway in a cancer cell. Additionally, an inhibition or reduction in the expression and/or functioning of BORG RNA may reduce or eliminate the protective effect of BORG RNA against post-stress cell death.

In some embodiments, the BORG inhibiting agent can include RNA interference (RNAi) polynucleotides to induce knockdown of a BORG RNA. For example, an RNAi polynucleotide can comprise a siRNA capable of inducing knockdown of a BORG RNA in a cancer cell.

RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve RNA degradation, however the biochemical mechanisms are currently an active area of research. Despite some mystery regarding the mechanism of action, RNAi provides a useful method of inhibiting gene expression in vitro or in vivo.

As used herein, the term "dsRNA" refers to siRNA molecules or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response.

As used herein, the term "RNAi construct" is a generic term used throughout the specification to include small interfering RNAs (siRNAs), hairpin RNAs, and other RNA species, which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

The choice of promoter and other regulatory elements generally varies according to the intended host cell. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The RNAi constructs contain a nucleotide sequence that hybridizes under physiologic conditions of the cell to the nucleotide sequence of at least a portion of the RNA transcript (e.g., BORG long non-coding RNA) for the gene or functional RNA to be inhibited (i.e., the "target"). The double-stranded RNA need only be sufficiently similar to natural RNA that it has the ability to mediate RNAi. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA or functional RNA is degraded by the nucleases in the protein complex. In a particular embodiment, the 21-23 nucleotides siRNA molecules comprise a 3' hydroxyl group.

The siRNA molecules can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In other embodiments, the RNAi construct can be in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects, which may be caused by the sequence-independent dsRNA response.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Such hairpin RNAs are engineered in cells or in an animal to ensure continuous and stable suppression of a desired gene. It is known in the art that siRNAs can be produced by processing a hairpin RNA in the cell.

In yet other embodiments, a plasmid can be used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an exemplary vector for bi-directional transcription of a transgene to yield both sense and antisense RNA transcripts of the same transgene in a eukaryotic cell. Accordingly, in certain embodiments, the a recombinant vector can have the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO01/68836 and WO01/75164.

Examples of RNAi constructs that specifically recognize a particular gene or a particular non-coding RNA, can be selected using methodology outlined in detail above with respect to the selection of antisense oligonucleotide. Similarly, methods of delivery for RNAi constructs include are well known in the art.

In some embodiments, a lentiviral vector can be used for the long-term expression of a siRNA, such as a short-hairpin RNA (shRNA), to knockdown expression of BORG RNA in cancer cells overexpressing BORG. Although there have been some safety concerns about the use of lentiviral vectors for gene therapy, self-inactivating lentiviral vectors are considered good candidates for gene therapy as they readily transfect mammalian cells.

The Examples below show that shRNA non-viral vector constructs are effective in the shRNA-mediated knock down of BORG RNA in mammalian cells to reduce the cellular level of BORG RNA to almost undetectable levels. shRNA constructs can be designed as described by Chang et al. (2006) *Lessons from Nature: microRNA-based shRNA libraries*. C Nat. Biotechnol 27, 275-280. For example, shRNA non-viral constructs covering the regions in the vicinity of nucleotides 80, 184, and 941 (SEQ ID NOs: 1, 2 and 3, respectively) of BORG RNA can be created to downregulate BORG RNA expression. Each hairpin sequence can be cloned into pGeneclip vectors containing neomycin/G418 resistance gene (Promega) and the accuracy of the sequence of the inserted construct can be verified by sequencing.

Moreover, it will be appreciated that other antibodies, small molecules, and/or peptides that reduce or inhibit BORG expression and/or activity in cancer cells can be use as a BORG inhibiting agent in accordance with the method described herein. These other BORG inhibiting agents can be administered to cancer cells of a subject at an amount effective to inhibit BORG expression and/or activity, c-MET induction, and/or NFkB pathway induction in the cancer cells of the subject.

In other embodiments, the BORG inhibiting agent can be used in combination and adjunctive therapies for inhibiting cancer cell proliferation and growth. The phrase "combination therapy" embraces the administration of the BORG inhibiting agent and an additional therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). The phrase "adjunctive therapy" encompasses treatment of a subject with agents that reduce or avoid side effects associated with the combination therapy of this application.

A combination therapy is intended to embrace administration of these BORG inhibiting agent in a sequential manner, that is, wherein different therapeutic agents are administered at a different time, as well as administration of the BORG inhibiting agent, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of therapeutic agents can be effected by an appropriate routes including, but not limited to, oral routes, intravenous routes, intramuscular routes, and direct absorption through mucous membrane tissues. The therapeutic agents can be administered by the same route or by different routes. The sequence in which the therapeutic agents are administered is not narrowly critical.

Combination therapy also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at a suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments, the BORG inhibiting agent can be administered with an anti-cancer agent that induces stress in the cancer cells. The stress applied to the cancer cell can include, for example, radiation therapy or ionizing radiation, thermal stress or thermal therapy, irreversible electroporation (IRE), oxidative stress, and anti-proliferative agents.

Radiation therapy may include both "sealed" and "unsealed" sources of therapeutic radiation including, but not limited to, ionizing radiation therapy, brachytherapy, sealed source radiation therapy, systemic radioisotope therapy, unsealed source radiotherapy, radionuclide therapy, external beam radiation therapy, radiation surgery, charged-particle radiotherapy, neutron radiotherapy, x-ray therapy, and cobalt therapy.

Thermal stress or therapy can include focused ultrasound (FUS or HIFU), radiofrequency, infrared sauna, microwave heating, induction heating, magnetic hyperthermia, infusion of warmed liquids, or direct application of heat. The thermal stress can include local hyperthermia and/or regional hyperthermia. The thermal stress or thermal therapy can also include exposure to sub-lethal heat. For example, a hyperthermia modality may heat a cancer cell or microorganism too much lower therapeutic temperatures (in general <45° C.) compared to other tissue ablation techniques. For instance, the elevation above a normal body temperature of 37° C. typically will fall within a range of 42° C. to 45° C.

Irreversible electroporation uses a series of microsecond electrical pulses instead of extreme heat, freezing, radiation or microwave energy—to permanently open cell membranes in cancerous tumors. Once the cell membrane pores are opened, the death of the targeted cancer cells is induced. Surrounding veins, nerves and ducts within the targeted area are largely unaffected by the process around them, providing a compelling tool for procedures in difficult-to-treat parts of the body.

The exposure to stress may also be imaged guided. For example, clinical HIFU procedures are typically image-guided to permit treatment planning and targeting before applying a therapeutic or ablative level of ultrasound energy. When MRI is used for guidance, the technique is sometimes called Magnetic Resonance-guided Focused Ultrasound, often shortened to MRgFU. When ultrasonography is used, the technique is sometimes called Ultrasound-guided Focused Ultrasound, often shortened to USgFUS.

The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agents available in commercial use, in clinical evaluation and in pre-clinical development, which could be included in this application by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

A cancer cell can be pretreated with a cell-sensitizing composition comprising the BORG inhibiting agent prior to exposure to stress. For example, a cell-sensitizing composition may be administered to a neoplastic cell for an amount of time before the cancer cell is exposed to stress. Alternatively, a cell-sensitizing composition can be administered concomitantly with the exposure of the neoplastic cell or microorganism to stress.

A subject having cancer, tumor, or at least one cancer or tumor cell, may be identified using methods known in the art. For example, the anatomical position, gross size, and/or cellular composition of cancer cells or a tumor may be determined using contrast-enhanced MRI or CT. Additional methods for identifying cancer cells can include, but are not limited to, ultrasound, bone scan, surgical biopsy, and biological markers (e.g., serum protein levels and gene expression profiles). An imaging solution comprising a cell-sensitizing composition of the present invention may be used in combination with MRI or CT, for example, to identify cancer cells.

The location(s) where the cell-sensitizing composition comprising the BORG inhibiting agent is administered to the subject may be determined based on the subject's individual need, such as the location of the cancer cells (e.g., the position of a tumor, the size of a tumor, and the location of a tumor on or near a particular organ). For example, the cell-sensitizing composition may be injected directly (i.e., intratumorally) into a tumor. Alternatively, the cell-sensitizing composition may be injected intravenously into the subject. It will be appreciated that other routes of injection may be used including, for example, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal routes.

The compositions and methods of the application will now be described in greater detail in the following non limiting Example.

EXAMPLE

BORG is Induced in Response to Stress and is Necessary for Post-stress Survival

Figure 4A:
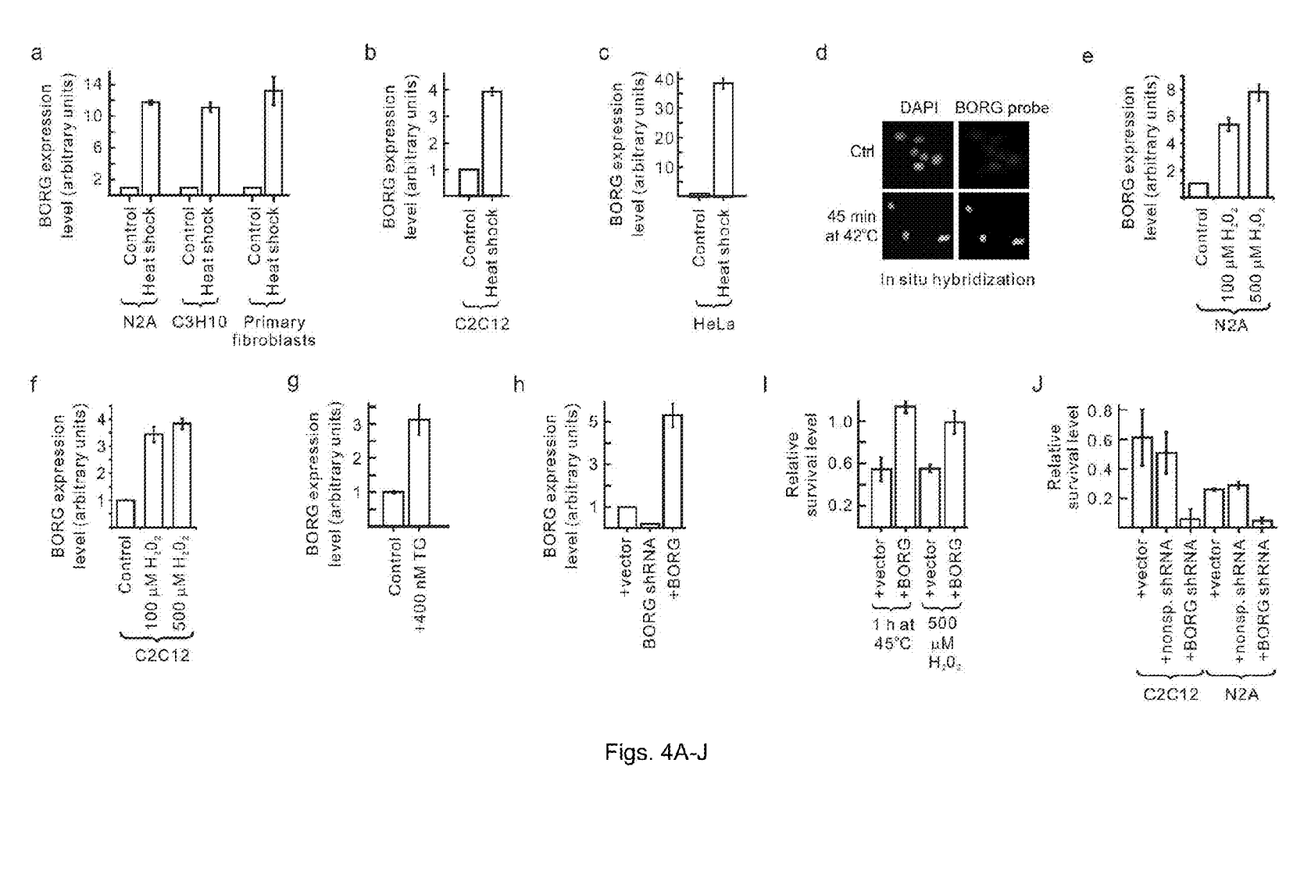

As shown in FIGS. 4A-C, the level of BORG expression increases in response to heat shock in N2a mouse neuroblastoma cells, C3H10 mouse fibroblasts, primary mouse fibroblasts, mounst myoblasts C2C12 cells and human HeLa cells. FIGS. 8E-F show that BORG is also induced in response to ER stress (induced by the addition of Thapsigargin, TG). Cell lines transfected by a BORG expression becotr or a vector expressing an shRNA against BORG (FIG. 4H) were used in a MTT cell survival assay to determine if the overexpression of BORG blocks post-stress cell death in C2C12 cells. It was shown that vector transfected, control cell lines exhibit close to 50% cell death after an hour long heat shock or oxidative stress, the BORG overexpressing cells are almost 100% alive (FIG. 4I). It was further shown that while vector transfected or control cells transfected with a non-specific shRNA show ~50%-30% survival after heat stress in C2C12 and N2A cells, respectively, the survival level of BORG knock down cells is ~5%. The similarity of results obtained in multiple cell lines and in response to multiple stress types suggests the generality of the protective effect of BORG against cell death BORG Expression Level is Increased in Tumor Tissue Compared to Adjacent Normal Tissue Using RT-qPCR, we determined the BORG expression level in ten pairs of tumor tissue (M) and adjacent normal lung tissue (N) from non-small cell lung cancer patients. As shown in FIG. 2, the level of BORG was noticeably greater in the tumor tissue compared to the adjacent normal lung tissue in 5 of the 10 patient samples.

BORG Expression Level is Increased in the most Aggressive Cancers

Using RT-qPCR, we determined the BORG expression level in various human and mouse tumor cells lines. FIG. 3(A) shows a set of three mouse breast cancer cell lines (67NR, 4T07, and 4T1) in increasing level of malignancy. The level of BORG is highest in the most aggressively metastatic tumor cells. Cells show especially high levels of aggressiveness when cultured in rigid versus the compliant three dimensional culture systems. The three human lung cell lines correspond to normal lung epithelium (NL20), primary tumor cells (A549) and metastatic tumor cells (H1650). Similar to the case with breast cancer cell lines, the level of BORG is highest in metastatic cells. FIG. 3(B) indicates a rise in the level of BORG in response to TGFb in mammary epithelial cells transformed with EGFR. Treatment with TGFb results in a highly aggressive metastatic phenotype in these cells.

Figure 1A:
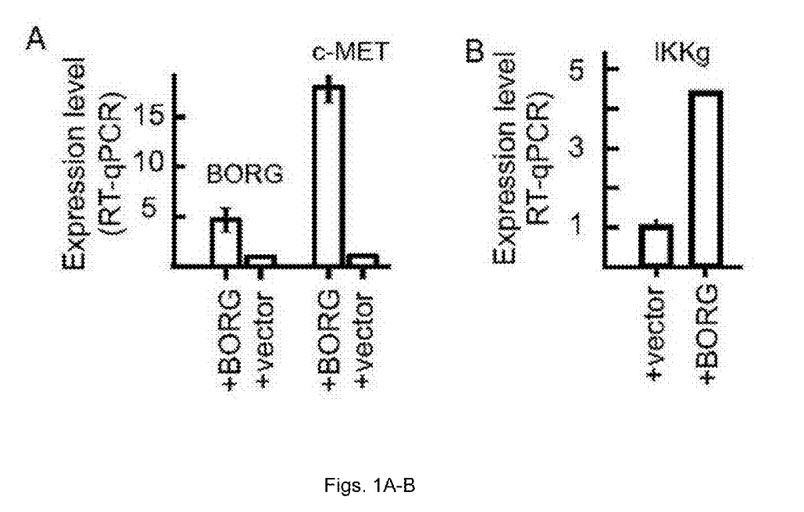

BORG Overexpression Results in the Induction of the c-METproto-oncogene and the NFkB Pathway We determined the expression levels of BORG and c-MET in vector transfected (+vector) and BORG overexpressing cells (+BORG) using RT-qPCR assays. As shown in FIG. 1A, BORG overexpression resulted in an increase in the expression level of c-MET compared to the control. We further determined the expression level of the regulatory subunit of IKB kinase (IKK), the inducer of the NFkB pathway. As shown in FIG. 1B the expression level of IKK is increased ~4 fold in BORG overexpressing cells compared to the vector transfected control. Taken together, the above results suggest that BORG overexpression in cells results in strong induction of the c-MET proto-oncogene and potentially, the NFkB pathway.

shRNA Construct Against BORG

Figure 5A:
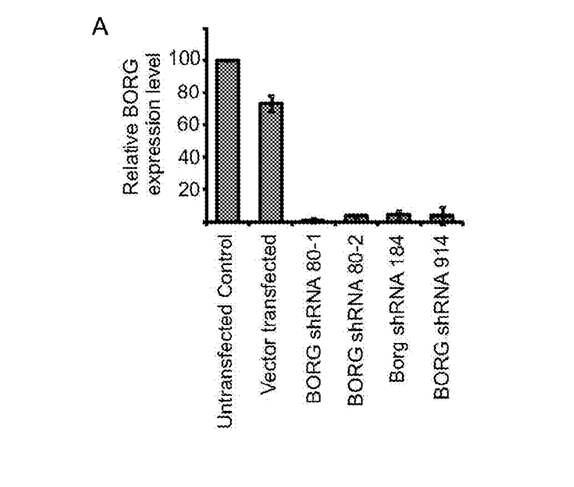
Figure 5B:
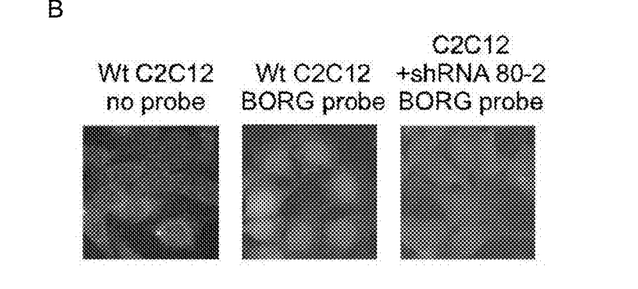
Figure 5C:
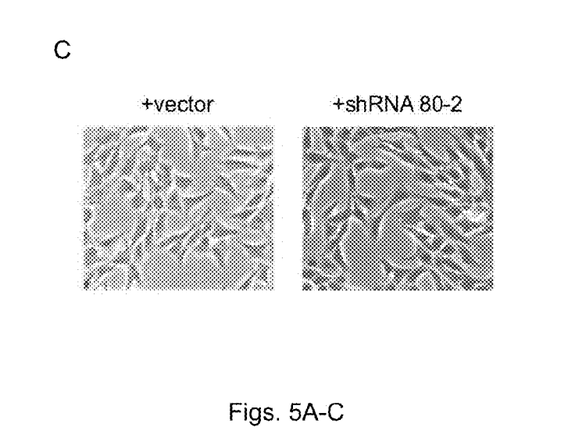

We used 4 different shRNA non-viral constructs covering the regions in the vicinity of nucleotides 80, 184, and 941 of BORG RNA to knockdown the level of expression of BORG in mammalian cells. FIG. 5A shows a reduction of BORG expression in all four stable knock down C2C12 cell lines vs. controls. Each knock down cell line is derived from a single stably transfected cell. Additionally, In situ hybridization was used to indicate the loss of nuclear signal in cells transfected with shRNA construct against BORG (FIG. 5B). A very low cellular level of BORG is compatible with viability under normal growth conditions. FIG. 5C shows a phase contrast image depicting BORG knock down C2C12 cells stably transfected with shRNA 80 (SEQ ID NO: 1).

Selection of shRNA Constructs

Each hairpin sequence was cloned into pGeneclip vectors containing neomycin/G418 resistance gene (Promega) and the accuracy of the sequence of the inserted construct was verified by sequencing. Three shRNA constructs targeting different regions of BORG were created to ensure efficient downregulation of expression and to help distinguish any off-target effects. The chosen sequences did not show significant complementarity to other regions of BORG or elsewhere in the mouse genome as determined by low stringency Blast searches. Three shRNA constructs containing scrambled sequences that did not show complementarity to any region of the mouse genome were designed as controls. The day before transfection, cells were plated at a density of $5\times10^4$ cells per well in a 24-well plate. 1 μg of vector DNA was transfected into the cells using lipofectamin 2000. To obtain stable cell lines, cells were transferred to media containing G418 (1 mg/mL) 48 hours after transfection, followed by 1-2 weeks of incubation until colonies appeared. For each DNA construct, 8 well-isolated colonies were selected using cloning disks. The cells were transferred into 12 well plates containing the G418-containing selection media. The cells were re-selected as described for N2a cells and then were allowed to grow followed by screening for BORG expression by RT-PCR. The sequence of the shRNA constructs is shown below.

shRNA construct covering the region in the vicinity of nucleotide 80 of BORG:

```
                                                         (SEQ ID NO: 1)
GAT CTC GCG TTG ACA GTG AGC GCG CCT CTC TCC TCG ATA AAG AGT AGT

GAA GCC ACA GAT GTA CTC TTT ATC GAG GAG AGA GGC ATG CCT ACT GCC

TCG A
``` shRNA construct covering the region in the vicinity of nucleotide 184 of BORG:

```
                                                         (SEQ ID NO: 2)
GAT CTC GCG TTG ACA GTG AGC GAT AGG CCA TGC TCC AGA TAT TAT AGT

GAA GCC ACA GAT GTA TAA TAT CTG GAG CAT GGC CTA GTG CCT ACT GCC

TCG A
``` shRNA construct covering the region in the vicinity of nucleotide 941 of BORG:

(SEQ ID NO: 3)
GAT CTC GCG TTG ACA GTG AGC GCT TGG TGA GGA ATG TAG GTA CTT AGT

GAA GCC ACA GAT GTA AGT ACC TAC ATT CCT CAC CAA ATG CCT ACT GCC

TCG A

While this application has been particularly shown and described with references to preferred embodiments thereof, it will be understood by those skilled in the art that various changes in form and details may be made therein without departing from the scope of the application encompassed by the appended claims. All patents, publications and references cited in the foregoing specification are herein incorporated by reference in their entirety.

agent comprising RNA interference (RNAi) polynucleotides to induce knockdown of a BORG RNA.

2. The method of claim 1, the therapeutically effective amount comprising the amount effective to inhibit NFkB activation in the cancer cells.

3. The method of claim 1, the therapeutically effective amount comprising the amount effective to inhibit expression and/or induction of c-MET in the cancer cells.

Having described the invention, the following is claimed:

1. A method of treating a BORG expressing cancer comprising:

administering a therapeutically effective amount of at least one BORG inhibiting agent to the BORG overexpressing cancer cells of the subject, the BORG inhibiting 4. The method of claim 1, wherein the cancer is selected from the group consisting of a lung cancer, a breast cancer, a brain cancer and a cervical cancer.

5. The method of claim 1, the cancer cells comprising primary tumor cells or metastatic tumor cells.

6. The method of claim 1, the RNA interference (RNAi) polynucleotides comprising a shRNA construct against BORG.

7. The method of claim 6, the shRNA construct having a nucleotide sequence of SEQ ID NO: 1, SEQ ID NO: 2, or SEQ ID NO: 3.

8. The method of claim 1, further comprising administering an anti-cancer agent in combination with the BORG inhibiting agent.

9. A method of treating a BORG expressing cancer comprising:
   administering therapeutically effective amounts of at least one BORG inhibiting agent and anti-cancer agent to the BORG overexpressing cancer cells of the subject, the BORG inhibiting agent comprising RNA interference (RNAi) polynucleotides to induce knockdown of a BORG RNA.

10. The method of claim 9, the therapeutically effective amount comprising the amount effective to inhibit NFkB activation in the cancer cells.

11. The method of claim 9, the therapeutically effective amount comprising the amount effective to inhibit expression and/or induction of c-MET in the cancer cells.

12. The method of claim 9, wherein the cancer is selected from the group consisting of a lung cancer, a breast cancer, a brain cancer and a cervical cancer.

13. The method of claim 9, the cancer cells comprising primary tumor cells or metastatic tumor cells.

14. The method of claim 9, the RNA interference (RNAi) polynucleotides comprising a shRNA construct against BORG.

15. The method of claim 14, the shRNA construct having a nucleotide sequence of SEQ ID NO: 1, SEQ ID NO: 2, or SEQ ID NO: 3.

16. The method of claim 8, wherein the anti-cancer agent is selected from the group consisting of radiation therapy or ionizing radiation, thermal stress or thermal therapy, irreversible electroporation (IRE), oxidative stress, and anti-proliferative agents.

* * * * *

SEQUENCE LISTING

```
<160> NUMBER OF SEQ ID NOS: 3

<210> SEQ ID NO 1
<211> LENGTH: 100
<212> TYPE: DNA
<213> ORGANISM: Artificial Sequence
<220> FEATURE:
<223> OTHER INFORMATION: Synthetic Construct

<400> SEQUENCE: 1
gatctcgcgt tgacagtgag cgcgcctctc tcctcgataa agagtagtga agccacagat      60 gtactctta tcgaggagag aggcatgcct actgcctcga                            100

<210> SEQ ID NO 2
<211> LENGTH: 100
<212> TYPE: DNA
<213> ORGANISM: Artificial Sequence
<220> FEATURE:
<223> OTHER INFORMATION: Synthetic Construct

<400> SEQUENCE: 2
gatctcgcgt tgacagtgag cgataggcca tgctccagat attatagtga agccacagat      60
gtataatatc tggagcatgg cctagtgcct actgcctcga                            100

<210> SEQ ID NO 3
<211> LENGTH: 100
<212> TYPE: DNA
<213> ORGANISM: Artificial Sequence
<220> FEATURE:
<223> OTHER INFORMATION: Synthetic Construct

<400> SEQUENCE: 3
gatctcgcgt tgacagtgag cgcttggtga ggaatgtagg tacttagtga agccacagat      60
gtaagtacct acattcctca ccaaatgcct actgcctcga                            100
```